United States Patent [19]

Pinto

[11] Patent Number: 5,173,513
[45] Date of Patent: Dec. 22, 1992

[54] METHANOL SYNTHESIS

[76] Inventor: Alwyn Pinto, 18 Cambridge Road, Linthorpe, Middlesbrough, Cleveland, England

[21] Appl. No.: 668,905

[22] Filed: Mar. 13, 1991

Related U.S. Application Data

[63] Continuation-in-part of Ser. No. 494,491, May 13, 1983, abandoned, which is a continuation of Ser. No. 296,243, Aug. 24, 1981, abandoned.

[30] Foreign Application Priority Data

Sep. 4, 1980 [GB] United Kingdom ............... 8028568
Jan. 22, 1981 [GB] United Kingdom ............... 8101950

[51] Int. Cl.$^5$ ............................................. C07C 27/06
[52] U.S. Cl. .................................. 518/704; 518/702; 518/703; 518/705; 518/711
[58] Field of Search ............... 518/704, 703, 702, 711, 518/705

[56] References Cited

FOREIGN PATENT DOCUMENTS 0047596 3/1982 European Pat. Off. ............ 518/703

Primary Examiner—Howard T. Mars
Attorney, Agent, or Firm—Cushman, Darby & Cushman

[57] ABSTRACT

In producing methanol by the reaction of carbon monoxide and hydrogen, a starting gas deficient in hydrogen, e.g. as produced by coal gasification, is mixed with a hydrogen rich gas and fed to a synthesis loop where it is mixed with unreacted gas from the synthesis stage. A part stream of gas is taken from the loop. Either that part stream, or the gas in the loop prior to synthesis, is subjected to the catalytic shift reaction with steam. Carbon dioxide is removed from the gas taken from the loop to form the hydrogen rich stream.

20 Claims, 3 Drawing Sheets

METHANOL SYNTHESIS

This application is a continuation-in-part of my application Ser. No. 06/494,491 filed May 13, 1983 (now abandoned) entitled "Synthesis" which in turn was a continuation of my application Ser. No. 06/296,243 (now abandoned) filed Aug. 24, 1981 (now abandoned) entitled "Synthesis".

This invention relates to a process for the synthesis of methanol from a carbon oxide/hydrogen synthesis gas.

Methanol is often made from a gas obtained by the catalytic reaction of a gaseous or vaporisable hydrocarbon feedstock with steam. When such feedstocks contain at least 2 hydrogen atoms per carbon atom, the gas contains at least sufficient hydrogen for methanol synthesis and can be passed to the synthesis with no loss of pressure due to chemical treatment. It has been proposed to produce methanol from other feedstocks, such as natural gases containing much carbon dioxide and especially from heavier hydrocarbons, coal, coke or shale, which are deficient in hydrogen and also have to be gasified by partial oxidation. In those cases the raw synthesis gas is subjected to steps of catalytic shift reaction and carbon dioxide removal in order to correct the composition of the gas. Such steps are complicated and thermally not very efficient. Moreover, they introduce a substantial pressure-drop, as a result of which either the initial partial oxidation has to be operated at an uneconomically high pressure or else an undesirably high consumption of energy in gas compression is incurred. Examples of the shift reaction applied to carbon monoxide made by partial oxidation are to be found in UK patent specifications 770765 and 1309872 and in the article by Staege in Erdol-Erdgas-Zeitschrift 1976, 92, 381-387.

In the ensuing description a number of process steps will be referred to by proper names. These names are Registered Trade Marks or otherwise proprietary to companies making design data available under licence.

We have now devised a methanol production process in which some or all of the above defects arising from the use of a starting gas that is deficient in hydrogen can be avoided. It is also capable of dealing with hydrocarbons encountered in the synthesis gas or as by-products produced in the synthesis process.

In the present invention, the hydrogen-deficient starting gas can be derived from catalytic reforming of carbon dioxide rich natural gas or catalytic partial oxidation of hydrocarbons boiling at not over 200° C. It may be a by-product such as the off-gas from a basic oxygen steelmaking furnace. More conveniently it is derived from partial oxidation of a carbonaceous feedstock such as a gaseous hydrocarbon, volatilisable hydrocarbon, heavy oil such as crude oil or residual oil, solids such as coal, coke and shales and waste materials such as polymers and wood products. The pressure of this gas is preferably at least 10 bar abs., especially in the range 20 to 60 bar abs., and thus the gas can be provided by a partial oxidation step at a pressure high enough not to need compression. Suitable steps are those known by the names of Shell, Texaco, Lurgi and Shell-Koppers. Since, however, the process can minimise pressure losses, the gas can be provided by a partial oxidation at pressure under 10 bar abs. such as the Koppers-Totzek and Winkler processes, followed by compression to the preferred level.

Unless the hydrogen-deficient starting gas has been produced by catalytic reforming, it has usually been purified by removal of particles such as of dust, tar and carbon, usually by water-scrubbing and often with transfer of carbon to a hydrocarbon for recycle to the partial oxidation, and scrubbing with an absorbent liquid to remove carbon dioxide, and hydrogen sulphide and possibly other sulphur compounds such as carbonyl sulphide. There may also be a step of removing nitrogen oxides and hydrogen cyanide by catalytic or other treatment, and purifications other than by scrubbing could be used.

For the scrubbing, either of the two available classes of process can be used. In one class carbon dioxide, hydrogen sulphide, and carbonyl sulphide can be thoroughly removed. Until recently only the "Rectisol" process, using methanol as absorbent, was capable of this. "Rectisol" requires the gas to be cooled to −10° to −40° C., which usually entails an initial stage of methanol treatment to remove water before the cold removal of sulphur compounds. Other processes using for example absorbents based on tetramethylene sulphone, are available or under development. The other class, using absorbents such as the chemical and physical solvents (other than methanol) set out below, can remove carbon dioxide and hydrogen sulphide efficiently but not the refractory sulphur compounds. They have the advantage of being operable at temperatures in the range −10° to 100° C., but the refractory sulphur compounds have to be decomposed in a separate stage with formation of hydrogen sulphide, which is then removed as part of the purification of the starting gas. For the absorbent-scrubbing the pressure of the gas is preferably at the level indicated above. Apart from possibly passage of the starting gas through a bed of an absorbent for hydrogen sulphide, for example through a bed of zinc oxide or a molecular sieve, the gas passes to the synthesis with substantially no further purification.

In the process of the invention a hydrogen-rich gas is added to the starting gas to form make-up gas which is fed to a methanol synthesis loop wherein the make-up gas is mixed with recycle gas. The mixture of make-up gas and recycle gas is subjected to a catalytic shift reaction with steam, to convert carbon monoxide to carbon dioxide and hydrogen, and then subjected to a catalytic methanol synthesis step with incomplete conversion, thus producing reacted gas containing methanol and unreacted gas. Methanol is separated from said unreacted gas, and at least part of the unreacted gas is recycled as said recycle gas. A part stream of the unreacted gas, before or after addition of the make-up gas thereto, is taken from the loop and is subjected to a carbon dioxide removal step to give the aforesaid hydrogen-rich gas. At least part of this carbon dioxide removal step may be a purification stage in the production of the starting gas. In an alternative form of the process of the invention, instead of subjecting the mixture of make-up gas and recycle gas to the catalytic shift reaction before passing to the methanol synthesis stage, the catalytic shift reaction is effected on the part stream of unreacted gas taken from the loop before or after addition of the make-up gas thereto.

The starting gas suitably contains 20-80% by volume of carbon monoxide on a dry and carbon dioxide free basis. As derived from partial oxidation it commonly contains 10-50% by volume of hydrogen and up to 15%, especially up to 10%, by volume of methane, nitrogen and noble gases.

The invention is especially valuable when the said carbon monoxide content of the starting gas is over 50%, especially over 60% by volume, as for example in gas derived from partial oxidation of coal by the Koppers-Totzek or Shell-Koppers process. As a result of performing the shift reaction on gas that has been taken from the synthesis loop, or on the mixture of the make-up gas and recycle gas prior to methanol synthesis, the carbon monoxide content of the gas subjected to the shift reaction is at a level, especially under 45% by volume, at which simplifications to the shift stage can be made, for example use of a simple adiabatic reactor of combining shift with other reaction steps or providing an adequate steam to carbon monoxide level at a low steam to gas ratio, and good heat recovery can be obtained.

In the synthesis of methanol as normally practised from a mixture of carbon monoxide, carbon dioxide, and hydrogen, little if any shift reaction takes place during synthesis and thus to produce the hydrogen-rich gas, the unreacted gas from the synthesis stage must be subjected to the shift reaction in a separate step and then to carbon dioxide removal. If, however, the methanol synthesis is carried out in presence of steam, then shift will accompany synthesis and, to produce the hydrogen-rich stream, the unreacted gas remaining after methanol separation will require carbon dioxide removal but less, and possibly no, separate shift reaction.

When methanol synthesis is accompanied by shift reaction by adding steam to the synthesis gas about to enter the synthesis catalyst, the shift reaction can occur over a catalyst particularly formulated to withstand shift reaction conditions and possibly having only low if any methanol synthesis activity. The shift step can be carried out in a separate reactor or in the upstream-most bed or beds of a synthesis reactor or in an inlet portion of a bed containing shift catalyst followed by synthesis catalyst. Preferably the shift reaction takes place over a copper-containing catalyst, and as a result the shift outlet gas requires little or no adjustment of temperature before it enters the synthesis. Typically the steam to dry gas ratio of the gas is under 0.2 entering the shift step and under 0.02 leaving it.

Instead of subjecting the mixture of make-up gas and recycle gas to the shift reaction as indicated above prior to methanol synthesis, the shift stage may be effected on a stream of unreacted gas taken from the synthesis loop, before or after adding the make-up gas thereto. In this case the shift is most conveniently at an outlet temperature in the range 300°-550° C. and over an iron-chrome catalyst, owing to the still relatively high carbon monoxide content of the gas being treated. If the gas being treated contains compounds, such as methanol, that would form methane over such a catalyst, a zinc-chrome catalyst can be used.

Steam for the shift reaction is provided preferably by humidification with hot water from heat-exchange with reacted gas in the synthesis step. In this event the high grade heat in the gas leaving shift at 300°-550° C. is available for high pressure (40-140 bar) steam generation and the effect is to upgrade the heat recovered from the synthesis.

In order to carry out a shift stage in an adiabatic bed, with minimum steam consumption and maximum heat recovery, the conditions of initial carbon monoxide concentration in the gas mixture, steam to gas ratio and temperature are chosen preferably to give an outlet carbon monoxide concentration in the range 3-18% by volume on a dry basis, before carbon dioxide removal. If the synthesis can be operated with a correspondingly low ratio of hydrogen to carbon oxides, concentrations of carbon monoxide of over 10% by volume in the shifted gas are preferred. Thus a starting steam to total gas ratio in the range 0.4-0.6 and an outlet temperature over 400° C. are very suitable.

The shift step can be simplified by limiting the extent of shift to the minimum that will provide hydrogen for the synthesis. It can thus be advantageous overall to operate the synthesis at what would normally be regarded as a deficiency of hydrogen. For methanol synthesis it has been customary to operate with a synthesis gas having such a composition that "R" is at least 2, possibly up to 15 or more, where $$R = [H_2 - CO_2]/[CO + CO_2]$$

where $H_2$, $CO_2$ and $CO$ represent the molar proportions of hydrogen, carbon dioxide and carbon monoxide respectively in the synthesis gas. In the present process R is preferably in the range 0.8-2.0, especially 1.0-1.8. For methanol synthesis in absence of added steam, since the synthesis reaction removes carbon oxides and hydrogen on the basis of $R = 2$, the unreacted gas after separation of methanol is still richer in carbon monoxide and it is necessary to use shift but this can be incomplete and a simple adiabatic bed can be used. If steam is added to the gases entering methanol synthesis the value of R does not change but owing to the shift reaction the hydrogen to carbon monoxide ratio increases and if it exceeds 2.0, after carbon dioxide removal the unreacted gas is thus enriched in hydrogen. A steam addition sufficient to produce an hydrogen to carbon monoxide ratio in the range 2.5-5.0 provides a suitable balance of methanol synthesis and shift and can make separate shift unnecessary. The intermediate case of separate shift to give a hydrogen to carbon monoxide ratio of 0.8-2.0, especially 1.0-1.8, and further shift by adding steam to the synthesis gas is preferred when the carbon monoxide content of the starting gas is over 50% by volume.

However if desired, a second stage, of low temperature shift (200°-260° C.) over a copper-containing catalyst, can follow a stage at 300°-450° C. Such a catalyst does not cause methane formation. By low temperature shift, an outlet carbon monoxide content in the range 0.2-3.0% can be readily attained and an export hydrogen stream produced, as described below.

The shift stage may be a separate step or may be part of another step. Thus if the gas processed to give the hydrogen-rich stream contains a hydrocarbon (which term includes a hydrocarbon derivative), it may be processed by reaction with steam over a catalyst in conditions such that the hydrocarbon is converted to carbon oxides and hydrogen. Preferred conditions include a temperature over 550° C., especially in the range 600°-900° C. and a steam to hydrocarbon carbon molar ratio of at least 2, especially in the range 3-10. Since the reaction of steam with a hydrocarbon is endothermic, the necessary heat can be provided for example by one or more times heating the steam/gas mixture and passing it over a catalyst, or by external heating (the catalyst being contained in tubes supported in a furnace) or by internal heating by added oxygen, in any event aided by any simultaneous shift reaction. The catalyst is typically one or more metals from Group VIII of the Periodic Table, especially nickel or cobalt, on a refractory support. Depending on the composition of the gas processed in this step and of hydrogen content required, the hydrocarbon/steam reaction step can provide enough hydrogen to make a separate shift reaction unnecessary. Alternatively such a hydrocarbon/steam reaction step may be followed by one or more steps of shift reaction.

The said hydrocarbon can enter in from various sources; for example it may be formed from side reactions accompanying the methanol synthesis or it may be present in the starting gas. Thus the gasification step used in the production of the starting gas, such as the Lurgi process, may be operated in conditions such that methane is present in the raw gas. Those conditions include especially a temperature in the range 900°–1700° C. and/or a pressure in the range 10–120 bar abs. The methane content of such a raw gas is typically in the range 1–20%, especially 4–10%, by volume on a dry basis. As a result of removal of carbon monoxide and hydrogen by methanol synthesis and of carbon dioxide removal steps, the methane content of the gas processed to give the hydrogen-rich gas is typically higher than this by a factor of 1.5–3.0.

After such a hydrocarbon/steam reaction stage, the hydrocarbon content, calculated as equivalent methane, of the hydrogen-rich stream is typically less than 5%, especially under 1%, by volume on a dry basis.

In the present invention the shift reaction is effected after diluting the starting gas with an added gas, i.e. the hydrogen rich gas and recycle gas. One effect of processing the carbon monoxide-containing gas in the presence of an added gas is to make it possible to carry out the shift step at a relatively high steam to carbon monoxide ratio but a relatively low steam to total dry gas ratio. The same applies to the steam/hydrocarbon reaction. As a result most or all the required steam can be introduced by contacting with hot water and little if any need by introduced as steam. Thermal efficiency is therefore improved and the expense of steam generation and water purification is decreased. The following Table A illustrates the effect. In this table, the "steam" is additional to the "$H_2O$", which represents residual water vapour in the gas respectively before steam addition or after steam removal.

cess and converted to wanted products or recovered in a form in which they can be used as fuel. As a result, discharge of large volumes environmentally objectionable effluents can be avoided. It is already known to return to the feedstock partial oxidation effluents such as carbon black, tar and phenolic liquors, if these are formed.

The hot water for the direct contacting is provided preferably by direct contacting with hot steam-containing gases, for example as produced by the shift or steam hydrocarbon reaction and/or by indirect heat exchange with reacted synthesis gas.

In order to produce the hydrogen-rich gas stream, the stream taken from the loop is subjected to a carbon dioxide removal step. As indicated above, this step can be a separate one or can be part of the purification stage of the starting gas. If desired part of the carbon dioxide can be removed in a separate step and the carbon dioxide removal step in the purification of the starting gas can remove further carbon dioxide. If two carbon dioxide removal steps are used, they can be linked to a common regenerator, if the absorbent is the same.

In the carbon dioxide removal step, the so-called "chemical" solvents can be used, such as ethanolamines or potassium carbonate, especially in the established processes such as "Amine Guard", "Benfield", "Benfield-DEA", "Vetrocoke" and "Catacarb", at any of the pressures contemplated for the process of the process of the invention.

For effective use of physical solvents the process pressure is preferably at least 20 bar abs.; however, since synthesis gas to be used over a copper-containing catalyst preferably contains 1–15%, especially 2–10%, by volume of carbon dioxide, the pressure need not be as high as in the production of ammonia synthesis gas in which substantially complete removal of carbon dioxide is needed. Provided enough hydrogen is present, any excess of carbon dioxide can be removed by reverse shift reaction accompanying synthesis.

As examples of physical solvents there may be mentioned: tetramethylene sulfone ("Sulfinol"); propylene carbonate (Fluor); N-methyl-2-pyrrolidone ("Purisol"); polyethyleneglycol dimethyl ether ("Selexol"); and

TABLE A

|  | Conventional process | | | | According to Invention | | | |
|---|---|---|---|---|---|---|---|---|
|  | inlet | | outlet | | inlet | | outlet | |
|  | kmol/h | % v/v | kmol/h | % v/v | kmol/h | % v/v | kmol/h | % v/v |
| CO | 7542 | 58.79 | 3500 | 20.73 | 6489 | 20.49 | 2447 | 6.85 |
| $CO_2$ | 1561 | 12.17 | 5603 | 33.19 | 2563 | 8.09 | 6605 | 18.49 |
| $H_2$ | 3512 | 27.38 | 7554 | 44.75 | 18367 | 58.00 | 22409 | 62.73 |
| $H_2O$ | 18 | 0.14 | 29 | 0.17 | 41 | 0.13 | 56 | 0.16 |
| $N_2$ | 195 | 1.52 | 195 | 1.16 | 4208 | 13.29 | 4208 | 11.78 |
| Total "dry" gas | 12828 | | 16881 | | 31667 | | 35725 | |
| Steam | 9300 | | 5247 | | 11807 | | 7750 | |
| Steam/CO v/v | 1.23 | | 1.5 | | 1.82 | | 3.17 | |
| Steam/dry gas v/v | 0.725+ | | 0.311 | | 0.373 | | 0.217 | |

+Of the ratio 0.725, 0.413 is added by contact with hot water, 0.312 by feeding steam.

At the inlet of shift a steam to carbon monoxide ratio of at least 1.0 (especially at least 1.5) and a steam to dry gas ratio under 0.6 (especially in the range 0.2–0.5) can be considered typical for the process of the invention when the shift step is not in the same cycle as synthesis.

For providing such steam the hot water is preferably a waste water stream from the process, particularly a condensate after shift but before carbon dioxide removal, or methanol distillation bottoms. Such waste water contains dissolved or suspended impurities, but by the direct contacting these are returned to the process.

methanol ("Rectisol").

The process is not, however, limited to solvent methods of carbon dioxide removal, as will be described below.

Whether or not the gas taken from the loop is subjected to shift step, the production of the hydrogen-rich stream preferably includes a physical process such as cryogenic fractionation, selective adsorption or membrane diffusion. Preferably the gas taken from the loop is divided into two streams, one of which is purified by removal of carbon dioxide by a solvent as described above, and the other is treated by such a physical method. If there is shift, it preferably precedes such division. The physical treatment step makes it possible to increase the purity of the hydrogen-enriched gas without the complication of low temperature shift. Such a physical treatment may provide a hydrogen stream that can be exported, for use in for example ammonia synthesis: indeed the invention includes such an integrated process for production of methanol and ammonia.

A more complete shift reaction is preferable when hydrogen is to be exported. The outlet carbon monoxide content, preferably in the range 0.2–3.0% by volume on a dry basis, can be achieved by multi-stage high temperature shift with removal of steam and carbon dioxide between stages. Preferably it is achieved by high temperature shift followed by low temperature shift, in which event there need be only cooling between the stages. The shifted gas is then cooled to below the dewpoint of steam, separated from condensed water and subjected to carbon dioxide removal. The resulting gas is pure enough to provide the hydrogen-rich stream to be mixed with the hydrogen-deficient starting gas as previously described. It is also suitable for conversion to ammonia synthesis gas. In a process in which the starting gas is provided by gasifying a feedstock with oxygen derived from air separation, ammonia synthesis gas can be produced by mixing the hydrogen-rich stream to be exported with nitrogen available from the air separation. Preferably this is done by washing the hydrogen-rich gas, after carbon dioxide removal, with liquid nitrogen, since this affords a very pure synthesis gas.

The aforesaid physical separation treatment is also highly valuable for removing non-reactive gases from the synthesis gas. Since most sources of carbon monoxide produce also small or fractional percentages of nitrogen and/or methane, and since methanol synthesis may also produce such percentages of methane, such non-reacting gases slowly build up in the synthesis loop; thus a purge of synthesis gas has to be maintained. In synthesis processes as usually operated a stream of recycle gas after product separation is purged and proposals have been made to treat it for recovery of carbon oxides and/or hydrogen. In the process of the invention a physical treatment as aforesaid of the gas taken from the loop is the most convenient way of removing the non-reacting gases.

One preferred form of the process of the invention comprises mixing a starting gas rich in carbon monoxide with a gas rich in hydrogen and a synthesis recycle gas, compressing the mixture, dividing the compressed mixture into two streams, processing one stream, by steps including shift and carbon dioxide removal, to produce the gas rich in hydrogen, and passing the other stream to synthesis to produce methanol and the recycle gas. For such a process compression by up to 50% or even up to 20% suffices, as in a synthesis circulating pump, and acts upon both the stream used to produce the hydrogen rich stream and on the synthesis stream.

An alternative preferred sequence comprises mixing a starting gas rich in hydrogen and a synthesis recycle gas, compressing the mixture, passing the compressed mixture to synthesis to produce a liquid synthesis product and an unreacted gas, dividing the unreacted gas into two streams, passing one stream to steps to produce the gas rich in hydrogen and passing the other stream to the mixing point as the synthesis recycle gas. This form of the process requires more compression because the pressure of the gas entering such steps is lower to the extent of the pressure drop through the synthesis. If desired, an additional compressor for the hydrogen rich gas production circuit could be used.

In any process in which the starting gas has been compressed, the hydrogen rich gas or unreacted gas can be fed into the starting gas upstream of the compressor used.

The methanol synthesis may be by any suitable process. The methanol synthesis catalyst typically contains metallic copper as its active constituent, with an oxidic support material. The support usually contains also zinc oxide and/or one or more further oxides such as of chromium or metals from Group II–IV of the Periodic Table (especially aluminium) and/or possibly, silver or oxides of boron, rare earth metals, vanadium or manganese. Catalysts not containing copper can be used, but are not preferred because a higher synthesis pressure and temperature are needed.

The synthesis may be over a catalyst in tubes surrounded by a coolant or in the space around tubes containing coolant. The coolant may be for example pressurised water or a mixture of diphenyl and diphenyl ether; the pressurised water can be used as feed for a boiler or humidifier or, like the mixture, heat-exchanged in liquid form with suitable water to be fed to a boiler or humidifier. Alternatively the coolant water may be allowed to boil and the resulting intermediate pressure steam used as process feed or in an engine or condensed in indirect or direct heat exchange with pressurised water. In a second process the catalyst temperature can be controlled by heat exchange with cool feed gas passing through tubes in the catalyst bed or through the space surrounding catalyst-filled tubes. In a third process the catalyst bed can be in several parts with heat-abstraction by indirect heat exchange between the parts. Each part of the bed operates adiabatically and thus the construction of the reactor is simpler than for the first or second process. In a fourth, widely used, process, the temperature is controlled by injecting cool synthesis gas ("quench gas") into the hot reacting synthesis gas. Quench gas can be injected into mixing chambers between successive parts of a catalyst bed or successive reactor vessels. A very convenient system involves a single body of catalyst in which are disposed catalyst-free perforated hollow bars each having a sparger for introducing the quench gas, the bars being large enough in cross section for their interiors to constitute mixing zones and close enough together or to the catalyst bed walls to cause a substantial proportion of reaction mixture to pass through their interiors, as described in UK patent specification 1105614. The temperature of quench gas can be below 50° C., but thermal efficiency is better if it is at between 50° and 150° C. A composite reactor having quench cooling at 2–4 upstream levels and indirect heat exchange before the downstream-most bed also has advantages.

The volume space velocity of the flow of gas through the synthesis catalyst bed is typically in the range 5000–50000 $h^{-1}$. and is preferably fixed at a level such that the gas leaves the catalyst bed when the quantity of methanol formed has been sufficient to raise the gas temperature to the design level, which is under 300° C. and most preferably under 280° C. The methanol content of the reacted gas is preferably 2–8% and thus the pressure is preferably in the range 20–50, especially 35–45, bar abs. By operating at such a relatively low pressure the methanol production rate can be kept at a level such that the exothermic heat of synthesis is taken up by the gas (including quench gas) and need not be removed by indirect heat exchange in the synthesis reactor. Consequently simple reactors having one or more adiabatic catalyst beds such as those described in UK patent specification 1105614 can be used, instead of the steam-raising tubular reactors previously disclosed for using synthesis gas made by partial oxidation. Broadly speaking, the synthesis pressure is chosen such that the partial pressures of stoichiometric carbon oxides and hydrogen are of the same order as in synthesis gas made by steam/hydrocarbon reforming. Since the gas fed to the synthesis catalyst in the process of the invention typically contains less than 10% by volume of methane, nitrogen and noble gases and not more than stoichiometric hydrogen, unlike synthesis gas produced by steam reforming of methane (which typically contains 10–25% methane, and 20–40% excess hydrogen), the total pressure required is typically 50–80% of the corresponding process based on steam reforming. The invention thus makes possible a very attractive methanol production process based on partial oxidation, even when the partial oxidation step is at a low pressure and has to be followed by compression.

One effect of the step of the production of the hydrogen rich stream by taking a part stream of gas from the synthesis loop is that methanol synthesis can be operated at a considerbly lower ratio of recycled gas to fresh gas than has been usual, for example 1.5–3.0 instead of the more conventional 4–6. Another effect is that the proportion of gas taken from the synthesis loop to produce the hydrogen rich stream can be for example 15–30% of the total and so much higher than in conventional processes where the purge is typically 2–10% of the total; however, the bulk of the hydrogen in this purge is recovered.

BRIEF DESCRIPTION OF THE DRAWINGS

Preferred forms of the invention are represented as flowsheets in the accompanying drawings, in which.

Figure 1:
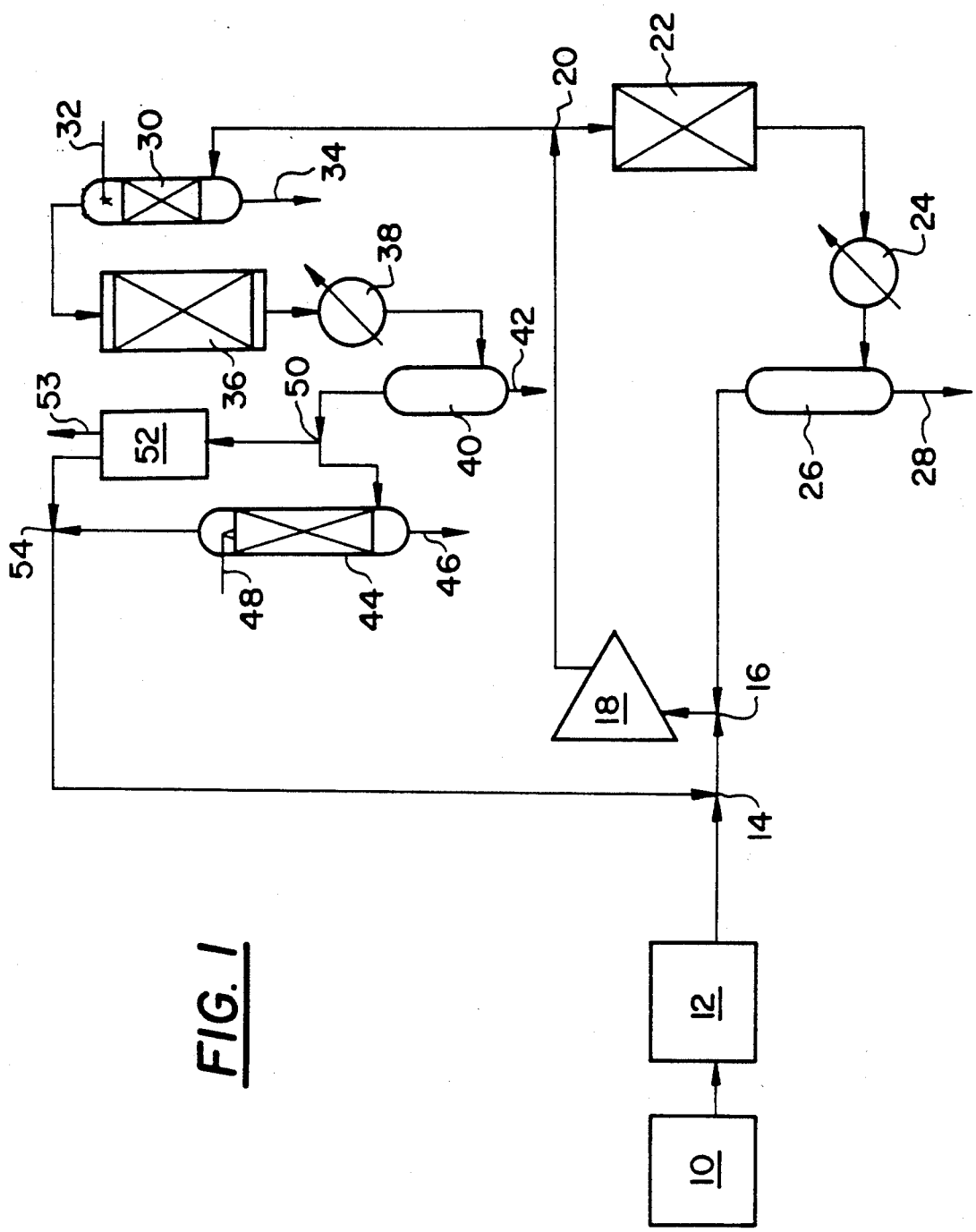
FIG. 1 shows a methanol production process in which a hydrogen rich gas is produced by applying shift and carbon dioxide removal in a side stream to a mixture of three gases.

In the process of FIG. 1 gasifier 10 reacts powdered coal with oxygen and a small quantity of steam to give a gas containing carbon monoxide and some hydrogen. Thus gas is freed from carbon, dust, hydrogen cyanide and nitrogen oxides in coarse purification treatments, compressed if necessary and then freed of hydrogen sulphide, carbonyl sulphide and carbon dioxide by contact with cold methanol. All these are generally indicated by purifier 12. The purified carbon monoxide rich gas is united at 14 with a hydrogen-rich stream to be described, then at 16 with a recycle gas stream to be described. The total mixture now has the design R value for methanol synthesis and is fed to the inlet of circulating pump 18, which increases its pressure by 10%. The compressed gas is divided at 20 into a synthesis stream and a shift stream. The synthesis stream is passed to synthesis reactor 22, which for simplicity is shown with a single catalyst bed but in practice may include multiple beds and various cooling means as set out above: it need not include internal indirect heat exchange with a coolant. Incomplete reaction to methanol takes place. The gas leaving reactor 22 is cooled at 24, which indicates generally preheating feed gas, heat recovery (with production preferably of hot water) and final cooling to below the dewpoint of methanol. Methanol is separated from the cooled gas in catchpot 26 and run off at 28 to distillation. Unreacted gas passing overhead from 26 is the recycle stream at point 16.

The shift stream from point 20 is warmed and humidified in packed tower 30 by hot water (heated at least partly at 24) fed in at 32, then fed to shift reactor 36, via a feed/effluent heat exchanger (part of 38, not shown separately). The resulting hot shifted gas is cooled in heat exchanger 38, which includes also high grade heat recovery as steam, boiler feed water heating and cooling to below the dewpoint of steam. Water is separated in catchpot 40 and run off at 42 to be reheated and fed again to tower 30, together with added water. The water depleted gas is divided at 50 into a dry-treatment stream (which is passed through pressure-swing adsorption unit 52 to remove methane, carbon monoxide, nitrogen and carbon dioxide at 53 and provide a pure hydrogen stream) and a wet treatment stream. The latter is contacted in tower 44 with a carbon dioxide absorbent solution fed in at 48. The charged solution is run off at 46 to a regenerator (not shown) and returned at 48. The overhead gas is united at 54 with the pure hydrogen, to form the hydrogen-rich stream at point 14.

Table 1 shows typical gas compositions and flow rates in the process, for producing about 2580 metric tons of methanol per day using the FIG. 1 flowsheet.

TABLE 1

| Position | Temp °C. | Press bar abs | Gas composition % v/v | | | | | | Flow rate kmol/h |
| --- | --- | --- | --- | --- | --- | --- | --- | --- | --- |
| | | | CO | $CO_2$ | $H_2$ | $CH_4 + N_2$ | $CH_3OH$ | $H_2O$ | |
| 12 outlet | 35 | 35 | 67.08 | 0.00 | 31.19 | 1.74 | 0.00 | 0.00 | 11239 |
| 18 outlet | 38 | 38.5 | 40.24 | 1.45 | 51.59 | 6.20 | 0.52 | 0.00 | 78252 |
| 22 inlet | 240 | 38 | 40.24 | 1.45 | 51.59 | 6.20 | 0.52 | 0.00 | 62602 |
| 22 outlet | 270 | 36 | 39.07 | 1.60 | 45.59 | 6.96 | 6.75 | 0.03 | 55729 |
| 26 overhead | 35 | 35 | 41.59 | 1.69 | 48.54 | 7.42 | 0.77 | 0.00 | 52323 |
| 28 product | 35 | 35 | 0.31 | 0.18 | 0.28 | 0.04 | 98.68 | 0.51 | 3406 |
| 36 outlet | 492 | 36.5 | 11.58 | 16.73 | 50.77 | 4.21 | 0.35 | 16.36 | 23050 |
| 44 to 54 | 35 | 36 | 17.04 | 2.00 | 74.72 | 6.19 | 0.05 | 0.00 | 12531 |
| 52 to 54 | 35 | 36 | 2.47 | 0.00 | 97.53 | 0.00 | 0.00 | 0.00 | 2160 |

Figure 2:
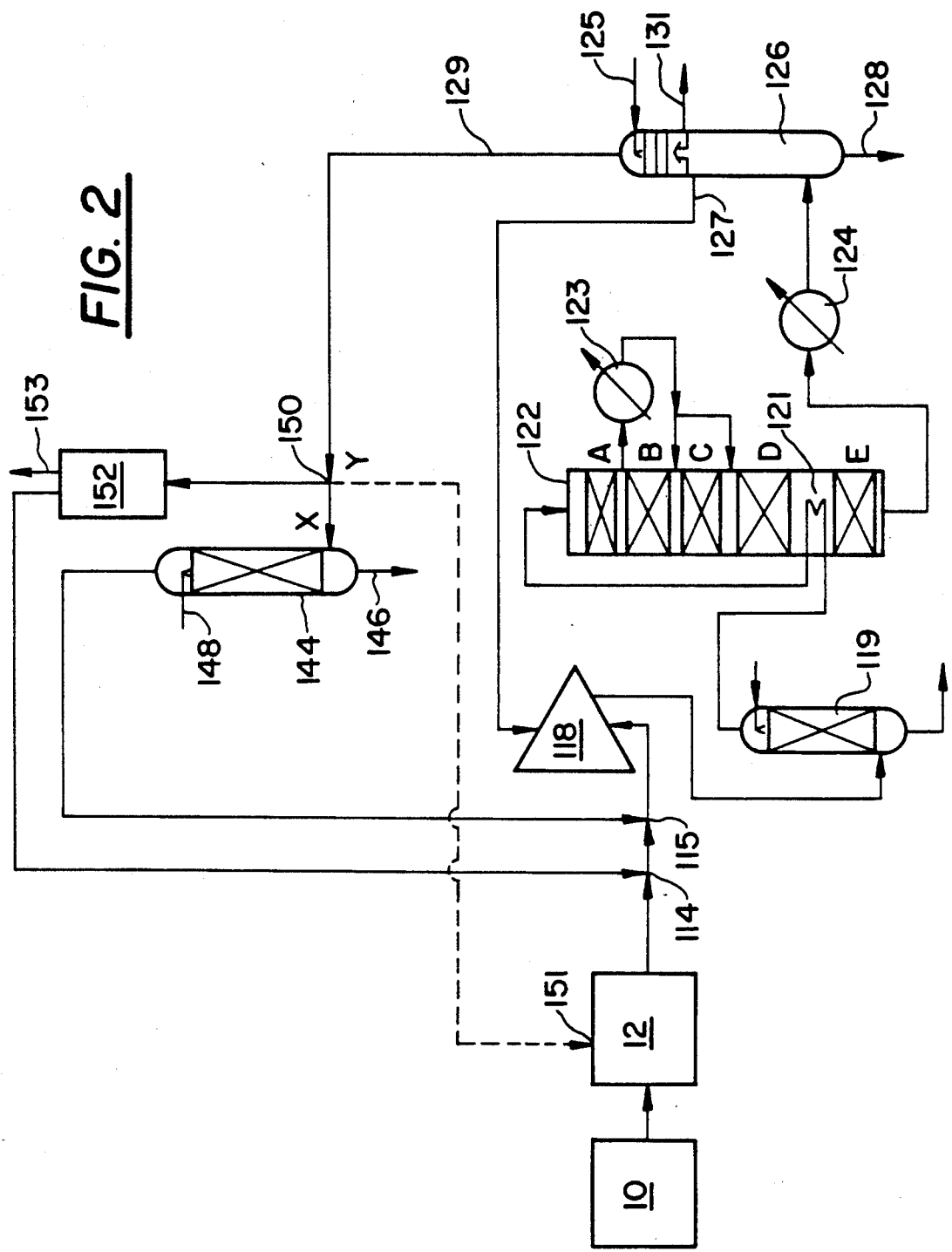
FIG. 2 shows a methanol production process in which shift is in the same cycle as methanol synthesis reactor but carbon dioxide removal is in a different cycle.

In FIG. 2 gasifier 10 reacts powdered coal with oxygen and a small quantity of steam to give a gas containing carbon monoxide and some carbon dioxide and hydrogen. This gas is freed of carbon, dust, hydrogen cyanide and nitrogen oxides in coarse purification treatments, then freed of hydrogen sulphide, carbonyl sulphide, and carbon dioxide by contact with cold methanol. These steps are indicated generally by purifier 12. A recycle stream to be described may be received at 151 after coarse purification but before carbon dioxide removal. The purified carbon monoxide rich gas is united at 114 with a first hydrogen-rich stream to be described, then at 115 with a second such stream which is instead of, or in addition to, the stream received at 151. The total mixture now has a hydrogen to carbon monoxide ratio lower than it is intended to use in methanol synthesis (unlike the corresponding mixture in the process of Table 2). It is fed to the inlet of circulating pump 118, which increases its pressure by about 10%. The compressed gas receives an addition of water vapour in packed tower saturator 119 in contact with hot water, which can include waste water from distillative purification of methanol and has been heated in a heater 123 or 124 to be described. The moist gas is then heated in heat exchanger 121 (by heat exchange with reacted methanol synthesis gas) to low temperature shift inlet temperature and passed into bed A of reactor 122, which bed contains low temperature shift catalyst. In bed A the shift reaction brings the hydrogen to carbon monoxide ratio to the design level but little if any methanol is synthesised. The gas leaving bed A is partly drawn off and cooled in heat recovery 123 (see below), partly passed through bed B, which is charged with methanol synthesis catalyst. Cooled gas from 123 is fed back partly into reactor 122 after bed B as a quench to lower the temperature, which has risen as the gas passes through bed B as a result of the exothermic methanol synthesis. The remainder of the cooled gas is fed back into reactor 122 after methanol synthesis bed C, again as a quench. The temperature rises yet again as the quenched gas passes through methanol synthesis bed D, but is then cooled by indirect heat exchange with shift inlet gas at 121. The cooled gas is reacted further in methanol synthesis bed E and led out to heat recovery and cooling steps indicated generally at 124. The heat recoveries 123 and 124 would in practice include for example (in decreasing order of heat grade): pressurised water heating (in a circuit including saturator 119); shift feed heating (preliminary to exchanger 121); and saturator water heating. In addition 124 includes cooling to below the dewpoint of methanol, whereafter liquid crude methanol is separated in the lower section of catchpot 126 and run off at 128 to distillative purification (not shown). Unreacted gas passing upwards in catchpot 126 is for the most part led out at 127 as a direct recycle stream, which is fed to an intermediate level in circulating pump 118. The rest of the unreacted gas enters the upper section of catchpot 126 via a chimney-plate and therein is freed of residual methanol vapour by contact on trays with cold water fed in at 125. Aqueous methanol is run off 131 to distillative purification. The scrub-bed gas 129 is divided at 150. One stream from 150 is a wet purification stream (carbon dioxide removal), which is passed (path X) to absorption tower 144 and contacted therein with a regenerable solution such as potassium carbonate or physical solvent such as a dialkyl ether of polyethyleneglycol. (The regeneration means is not shown.) (Dotted path Y is an alternative to path X and feeds the scrubbed gas to point 151 in purifier 12. Then the carbon dioxide removal step in purifier 12 replaces item 144. If desired, paths X and Y could both be used.) The other stream from 150 is passed to dry purifier 152, which separates the first hydrogen stream, which is passed to mixing point 114, and a purge stream (methane, carbon dioxide, nitrogen, carbon monoxide, and noble gases) at 153. Item 152 can be for example a cryogenic, adsorptive or diffusive unit. Stream 153 is the purge by which non-reactive gases are removed from the process. Elements 146 and 148 correspond to elements 46 and 48, respectively.

Table 2 shows typical gas compositions and flow rates in the process, for producing about 2375 metric tons of methanol per day using the flowsheet of FIG. 2 (path X only).

TABLE 2

| Position | Temp °C. | Press bar abs | Gas composition % v/v | | | | | | Flow rate kmol/h |
|---|---|---|---|---|---|---|---|---|---|
| | | | CO | $CO_2$ | $H_2$ | $CH_4 + N_2$ | $CH_3OH$ | $H_2O$ | |
| 12 outlet | 35 | 35 | 67.04 | — | 31.22 | 1.74 | — | — | 11250 |
| 118 outlet | 35 | 38.5 | 34.45 | 10.83 | 51.00 | 3.09 | 0.61 | 0.02 | 70076 |
| 122 inlet | 210 | 38 | 32.90 | 10.34 | 48.70 | 2.95 | 0.58 | 4.52 | 73379 |
| A outlet | 240 | 37 | 28.76 | 14.48 | 52.85 | 2.95 | 0.58 | 0.38 | 73379 |
| E outlet | 270 | 36 | 26.89 | 15.73 | 48.42 | 3.22 | 5.24 | 0.50 | 67193 |
| 128 product | 35 | 35 | 0.18 | 1.65 | 0.42 | 0.03 | 88.16 | 9.57 | 3301 |
| 126 overhead | 35 | 35 | 28.27 | 16.46 | 50.90 | 3.39 | 0.96 | 0.03 | 63892 |
| 127 recycle | 35 | 35 | 28.27 | 16.46 | 50.90 | 3.39 | 0.96 | 0.03 | 44724 |
| 150 to 144 | 35 | 35 | 28.54 | 16.62 | 51.39 | 3.42 | — | 0.03 | 13289 |
| 150 to 152 | 35 | 35 | 33.55 | 2.02 | 60.41 | 4.02 | — | — | 11305 |
| 144 to 115 | 35 | 35 | 28.54 | 16.62 | 51.39 | 3.42 | — | 0.03 | 5695 |
| 152 to 114 | 35 | 35 | 5.81 | — | 94.19 | — | — | — | 2797 |
| 153 | 35 | 35 | 50.47 | 32.65 | 10.10 | 6.72 | — | 0.06 | 2899 |

About 2235 t/d of methanol are recoverable from 128 and about 140 t/d are recoverable from stream 131.

Figure 3:
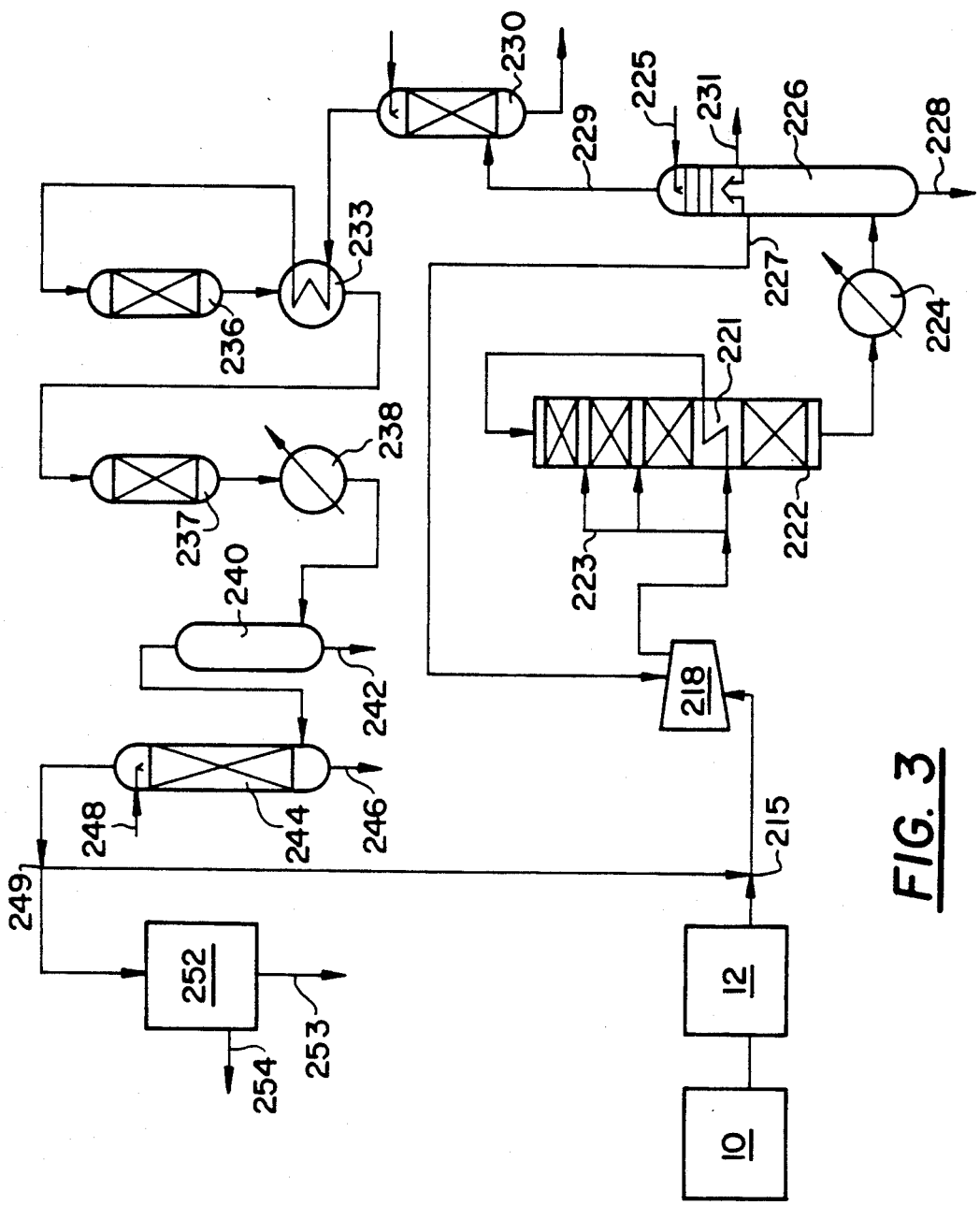
FIG. 3 shows the methanol synthesis section of an integrated process for producing methanol and ammonia.

In FIG. 3 gasifier 10 and purifier 12 are as in FIG. 2. The purified carbon monoxide rich gas from 12 is united at 215 with a hydrogen-rich stream to be described and passed to the inlet of circulating pump 218, which increases its pressure by about 10%. The total mixture has a hydrogen to carbon monoxide ratio sufficient for methanol synthesis. Part of it is heated at 221 by indirect heat exchange with reacted synthesis gas to synthesis inlet temperature and passed into the first catalyst bed of reactor 222. The remainder, possibly after warming, is fed between the catalyst beds as quenches 223. The gas reacts in a first series of catalyst beds and is cooled between the beds by the quench gas feeds 223. After the first series of beds the gas is cooled by indirect heat exchange at 221 and finally reacted in the lower-most bed in reactor 222. It is then led out to heat recovery and cooling steps indicated generally by 224, which are the same as in the process of FIG. 2. Liquid methanol is separated in the lower section of catchpot 226 and run off at 228. Unreacted gas passing upwards in catchpot 226 is for the most part led off from the lower section as direct recycle stream 227, which is fed to an intermediate level in circulating pump 218. The rest enters the upper section of catchpot 226 via a chimney plate and therein is freed of residual methanol vapour by contact on trays with cold water fed in at 225. Aqueous methanol is run off at 231 to distillative purification. The scrubbed gas 229 receives an addition of steam by saturation with hot water at 230, is heated to shift inlet temperature at 233 and is passed into high temperature shift reactor 236. Here it reacts exothermally, whereafter it is cooled, by external heat recovery as inter alia hot water for saturator 230 and by heat exchange at 233 with feed gas, to the inlet temperature of low temperature shift reactor 237. Here the shift reaction is substantially completed. The resulting gas is cooled at 238 with external heat recovery and then to below the dewpoint of water, which is separated in catchpot 240 and run off at 242. The resulting water-depleted gas is contacted in 244 with a carbon dioxide absorbent solution fed in at 248. The loaded absorbent is passed out at 246 to a regenerator (not shown). The carbon dioxide depleted gas is divided at 249 into a first hydrogen rich stream which is recycled to 215 and a second hydrogen-rich stream, which is contacted at 252 with liquid nitrogen to give ammonia synthesis gas 253 and a discard stream 254. The ammonia synthesis section is conventional and is not shown.

The water fed to saturator 230 can include waste water from distillative purification of methanol and condensate from point 242, and is heated in a circuit including one or more of heat recoveries 224, 233 and 238 and others in items 10 and 12.

Table 3 shows typical gas compositions and flow rates in a process using the flowsheet of FIG. 3 for producing about 1900 metric tons of methanol per day and providing sufficient hydrogen via stream 253 to produce about 650 t/d ammonia. About 1817 t/d of methanol is recoverable via stream 228 and the remainder is recoverable from stream 231.

The following alternative forms of this process are to be noted:
(a) If desired, reactor 222 can be operated in the same way as reactor 122 of FIG. 2, so as to effect shift reaction in its first bed;
(b) If gasifier 10 produced a gas containing more methane, it would be desirable to insert a methane/steam reaction step between points 230 and reactor 236. Heater 233 would then provide only external heat recovery. Heat would be recovered from the product of that reaction step when cooling it to the inlet temperature of reactor 222.

What I claim is:

1. A process for the manufacture of methanol by the reaction of carbon monoxide and hydrogen comprising:
    a) purifying a starting gas containing carbon monoxide but deficient in hydrogen by a process including a carbon dioxide removal step,
    b) adding a hydrogen-rich gas to the starting gas before said carbon dioxide removal step,
    c) after said carbon dioxide removal step, feeding said mixture of the starting gas and said hydrogen-rich gas as make-up gas to a synthesis loop and therein mixing said make-up gas with recycle gas to form synthesis gas,
    d) subjecting said synthesis gas to a catalytic methanol synthesis step with incomplete conversion, thus producing reacted gas containing methanol and unreacted gas,
    e) separating methanol from said unreacted gas, and recycling at least part of said unreacted gas as said recycle gas,
    f) taking part of the unreacted gas, before or after addition of the make-up gas thereto, from said synthesis loop, and
    g) subjecting said unreacted gas taken from the loop to a catalytic shift reaction with steam, to convert carbon monoxide to carbon dioxide and hydrogen thus producing said hydrogen-rich gas.

2. A process according to claim 1 wherein, prior to subjecting the unreacted gas stream taken from the loop to the shift reaction, steam is added to the unreacted gas taken from the loop by contact of the unreacted gas taken from the loop with a stream of heated water.

3. A process according to claim 1 wherein the gas that has been subjected to the catalytic shift reaction is subjected to a further carbon dioxide removal step to form the hydrogen-rich gas before the latter is added to the starting gas.

4. A process according to claim 1 wherein water is separated from the gas subjected to the shift reaction and part of the resulting water-depleted gas is subjected to a pressure swing adsorption process giving a pure hydrogen stream which is added to the make-up gas before addition thereof to the synthesis loop.

5. A process according to claim 1 wherein the gas taken from the loop is unreacted gas before the addition of make-up gas thereto.

6. A process according to claim 1 wherein the unreacted gas taken from the loop contains a hydrocarbon or hydrocarbon derivative that was present in the starting gas or was formed in the synthesis step as a by-product, and the unreacted gas taken from the loop is reacted with steam over a catalyst at an outlet tempera-

TABLE 3

| Position | Temp °C. | Press bar abs | Gas composition % v/v | | | | | | Flow rate kmol/h |
|---|---|---|---|---|---|---|---|---|---|
| | | | CO | $CO_2$ | $H_2$ | $CH_4 + N_2$ | $CH_3OH$ | $H_2O$ | |
| 12 outlet | 35 | 35 | 64.35 | 4.00 | 29.98 | 1.67 | — | — | 10504 |
| 218 outlet | 35 | 38.5 | 32.19 | 3.06 | 59.10 | 5.20 | 0.39 | 0.06 | 41949 |
| 222 inlet | 240 | 38 | 32.19 | 3.06 | 59.10 | 5.20 | 0.39 | 0.06 | 41949 |
| 222 outlet | 270 | 36 | 29.85 | 3.43 | 53.59 | 5.89 | 7.13 | 0.11 | 37000 |
| 228 product | 35 | 35 | 0.28 | 0.44 | 0.39 | 0.04 | 97.28 | 1.57 | 2432 |
| 226 overhead | 35 | 35 | 31.93 | 3.64 | 57.33 | 6.30 | 0.79 | 0.01 | 34568 |
| 227 recycle | 35 | 35 | 31.93 | 3.64 | 57.33 | 6.30 | 0.79 | 0.01 | 20741 |
| 236 outlet | 464 | 33 | 4.79 | 15.95 | 47.25 | 3.67 | — | 28.33 | 23716 |
| 237 outlet | 265 | 31.8 | 0.65 | 20.09 | 51.39 | 3.67 | — | 24.19 | 23716 |
| 244 outlet | 35 | 31.3 | 1.15 | 1.00 | 91.10 | 6.51 | — | 0.24 | 13380 |
| 249 to 215 | 35 | 31.3 | 1.15 | 1.00 | 91.10 | 6.51 | — | 0.24 | 10704 |
| 249 to 252 | 35 | 31.3 | 1.15 | 1.00 | 91.10 | 6.51 | — | 0.24 | 2676 |
| 253 | 35 | 30 | — | — | 100.00 | — | — | — | 2438 | ture of at least 550° C. and with a steam to hydrocarbon carbon molar ratio of at least 2, whereby to convert said hydrocarbon or hydrocarbon derivative to hydrogen and carbon oxides at the same time as effecting said shift reaction.

7. A process for the manufacture of methanol by the reaction of carbon monoxide and hydrogen comprising:
   a) purifying a starting gas containing carbon monoxide but deficient in hydrogen by a process including carbon dioxide removal step,
   b) adding a hydrogen-rich gas to the starting gas stream before said carbon dioxide removal step,
   c) after said carbon dioxide removal step, feeding said mixture of the starting gas and said hydrogen-rich gas as make-up gas to a synthesis loop and therein mixing said make-up gas with recycle gas,
   d) subjecting the mixture of said make-up gas and recycle gas to a catalytic shift reaction with steam, to convert carbon monoxide to carbon dioxide and hydrogen, thus producing synthesis gas,
   e) subjecting said synthesis gas to a catalytic methanol synthesis step with incomplete conversion, thus producing reacted gas containing methanol and unreacted gas,
   f) separating methanol from said unreacted gas, and recycling at least part of said unreacted gas as said recycle gas, and
   g) taking part of the unreacted gas, before or after addition of the make-up gas thereto, from said synthesis loop as said hydrogen-rich gas.

8. A process according to claim 7 wherein, prior to subjecting the mixture of make-up gas and recycle gas to the shift reaction, steam is added to the mixture of make-up gas and recycle gas by contact of the mixture of make-up gas and recycle gas with a stream of heated water.

9. A process according to claim 7 wherein the unreacted gas taken from the loop is subjected to a further carbon dioxide removal step to form the hydrogen-rich gas before the latter is added to the starting gas.

10. A process according to claim 7 wherein part of the unreacted gas taken from the loop is subjected to a separation process giving a hydrogen stream which is added to the make-up gas before addition thereof to the synthesis loop.

11. A process according to claim 7 wherein the gas taken from the loop is unreacted gas before the addition of make-up gas thereto.

12. A process for the manufacture of methanol by the reaction of carbon monoxide and hydrogen comprising
   a) providing a starting gas that contains carbon monoxide but is deficient in hydrogen,
   b) adding a hydrogen-rich gas to the starting gas,
   c) feeding said mixture of the starting gas and said hydrogen-rich gas as make-up gas to a synthesis loop and therein mixing said make-up gas with recycle gas to form synthesis gas,
   d) subjecting said synthesis gas to a catalytic methanol synthesis step with incomplete conversion, thus producing reacted gas containing methanol and unreacted gas,
   e) separating methanol from said unreacted gas, and recycling at least part of said unreacted gas as said recycle gas,
   f) taking part of the unreacted gas, before or after addition of the make-up gas thereto, from said synthesis loop,
   g) subjecting said unreacted gas taken from the loop to a catalytic shift reaction with steam, to convert carbon monoxide to carbon dioxide and hydrogen thus producing a shifted gas, and
   h) subjecting said shifted gas to carbon dioxide removal to produce said hydrogen-rich gas.

13. A process according to claim 12 wherein, prior to subjecting the unreacted gas stream taken from the loop to the shift reaction, steam is added to the unreacted gas taken from the loop by contact of the unreacted gas taken from the loop with a stream of heated water.

14. A process according to claim 12 wherein water is separated from the shifted gas and part of the water-depleted shifted gas is subjected to a pressure swing adsorption process giving a pure hydrogen stream which is added to the make-up gas before addition of the latter to the synthesis loop.

15. A process according to claim 12 wherein the gas taken from the loop is unreacted gas before the addition of make-up gas thereto.

16. A process according to claim 12 wherein the unreacted gas taken from the loop contains a hydrocarbon or hydrocarbon derivative that was present in the starting gas or was formed in the synthesis step as a by-product, and the unreacted gas taken from the loop is reacted with steam over a catalyst at an outlet temperature of at least 550° C. and with a steam to hydrocarbon carbon molar ratio of at least 2, whereby to convert said hydrocarbon or hydrocarbon derivative to hydrogen and carbon oxides at the same time as effecting said shift reaction.

17. A process for the manufacture of methanol by the reaction of carbon monoxide and hydrogen comprising
   a) providing a starting gas that contains carbon monoxide but is deficient in hydrogen,
   b) adding a hydrogen-rich gas to the starting gas,
   c) feeding said mixture of the starting gas and said hydrogen-rich gas as make-up gas to a synthesis loop and therein mixing said make-up gas with recycle gas,
   d) subjecting the mixture of said make-up gas and recycle gas to a catalytic shift reaction with steam, to convert carbon monoxide to carbon dioxide and hydrogen, thus producing synthesis gas,
   e) subjecting said synthesis gas to a catalytic methanol synthesis step with incomplete conversion, thus producing reacted gas containing methanol and unreacted gas,
   f) separating methanol from said unreacted gas, and recycling at least part of said unreacted gas as said recycle gas,
   g) taking part of the unreacted gas, before or after addition of the make-up gas thereto, from said synthesis loop, and
   h) subjecting said unreacted gas taken from the loop to carbon dioxide removal thus producing said hydrogen-rich gas.

18. A process according to claim 17 wherein, prior to subjecting the mixture of make-up gas and recycle gas to the shift reaction, steam is added to the mixture of make-up gas and recycle gas by contact of the mixture of make-up gas and recycle gas with a stream of heated water.

19. A process according to claim 17 wherein part of unreacted gas taken from the loop is subjected to a separation process giving a hydrogen stream which is added to the make-up gas before addition of the latter to the synthesis loop.

20. A process according to claim 17 wherein the gas taken from the loop is unreacted gas before the addition of make-up gas thereto.

* * * * *